(12) United States Patent
Vera

(10) Patent No.: US 11,007,349 B2
(45) Date of Patent: May 18, 2021

(54) LOCKING LINE TAG

(71) Applicant: Elmer Vera, American Canyon, CA (US)

(72) Inventor: Elmer Vera, American Canyon, CA (US)

( * ) Notice: Subject to any disclaimer, the term of this patent is extended or adjusted under 35 U.S.C. 154(b) by 0 days.

(21) Appl. No.: 16/523,626

(22) Filed: Jul. 26, 2019

(65) Prior Publication Data
US 2020/0046945 A1 Feb. 13, 2020

Related U.S. Application Data

(60) Provisional application No. 62/764,256, filed on Jul. 26, 2018.

(51) Int. Cl.
| | |
|---|---|
| *A61M 25/02* | (2006.01) |
| *G09F 3/00* | (2006.01) |
| *A61B 90/94* | (2016.01) |
| *G09F 3/02* | (2006.01) |
| *A61M 5/14* | (2006.01) |

(52) U.S. Cl.
CPC ........... *A61M 25/02* (2013.01); *G09F 3/0295* (2013.01); *A61B 90/94* (2016.02); *A61M 5/14* (2013.01); *A61M 2025/028* (2013.01); *A61M 2205/60* (2013.01); *G09F 2003/0251* (2013.01); *G09F 2003/0269* (2013.01)

(58) Field of Classification Search
CPC . G09F 3/0295; G09F 2003/0251; G09F 3/205
USPC ............... 40/316, 672, 661.08, 322
See application file for complete search history.

(56) References Cited

U.S. PATENT DOCUMENTS

| | | | | |
|---|---|---|---|---|
| 2,652,647 | A | * | 9/1953 | Suciu ...................... G09F 15/00 40/661.08 |
| 3,263,820 | A | * | 8/1966 | McFadden ............ A61M 5/008 211/60.1 |
| 4,862,617 | A | * | 9/1989 | Cooke, Jr. ................. G09F 3/18 40/663 |
| 2005/0103949 | A1 | * | 5/2005 | Ross ................... A61M 5/1418 248/68.1 |
| 2013/0138044 | A1 | * | 5/2013 | Schuman .............. G09F 3/0295 604/174 |
| 2014/0252177 | A1 | * | 9/2014 | Vera .................... A61M 5/1418 248/68.1 |
| 2015/0272828 | A1 | * | 10/2015 | Pfanner .................. G06Q 50/22 604/404 |

\* cited by examiner

*Primary Examiner* — Kristina N Junge
(74) *Attorney, Agent, or Firm* — Antonio Papageorgiou; Lombard & Geliebter LLP

(57) ABSTRACT

A locking line tag is provided that includes an elongated sheet of material having a top, bottom, and opposing lateral sides between the top and bottom, the sheet further having a plurality of scored lines therein that when folded form a tubular structure with a panel at each of the top and bottom ends that interlock with each other and at least a pair of intermediate sections, each of the intermediate sections having a key slot therein that open to opposing lateral sides of the locking tag.

9 Claims, 20 Drawing Sheets

LOCKING LINE TAG

BACKGROUND OF THE INVENTION

The present application relates generally to an attachable tag and more specifically to a tag attachable to an intravenous (IV) line for easy and safe identification of intravenous medications commonly used in the hospital setting.

Despite advancement in modern medicine, the complexity associated with identification of multiple IV infusion remain unsolved. Generally, the intravenous line infusion identification remains chaotic and disorganized. As a result, drug incompatibility reaction, mislabeling, and confusion remain a big problem especially in the critical care setting. Accordingly, there is a need for marking or otherwise tagging lines that alleviate or ameliorate these types of problems.

SUMMARY OF THE INVENTION

This application generally relates to a labeled or writable locking line tag which, in at least one embodiment, includes of a strip of plastic or paper materials which then is scored/folded into three sections with a hole located midline. These folds form a rectangular parallelepiped figure/structure and secured at the ends with tape or interlocking flaps.

In at least one embodiment, a locking line tag is provided that includes an elongated sheet of material having a top, bottom, and opposing lateral sides between the top and bottom, the sheet further having a plurality of scored lines therein that when folded form a tubular structure with a panel at each of the top and bottom ends that interlock with each other and at least a pair of intermediate sections, each of the intermediate sections having a key slot therein that open to opposing lateral sides of the locking tag.

In at least one embodiment, the tubular structure is a rectangular parallelepiped.

In at least one embodiment, the elongated sheet is generally rectangular.

In at least one embodiment, the scored lines when folded form a tubular structure with at least three intermediate sections.

In at least one embodiment, the key slots are located on a pair of non-adjacent intermediate sections.

In at least one embodiment, the key slots are located on a pair of intermediate sections separated by one intermediate section.

In at least one embodiment, the top panel comprises a key tab and the bottom panel comprises a slit configured to receive the key tab and lock the top and bottom panels to each other.

In at least one embodiment, the key slots include a hole sized to create a friction fit with an IV line inserted into the key slot.

In at least one embodiment, the locking tag of claim 1, further has at least one interior key slot therein.

In at least one embodiment, the interior key slot has a slit between a pair of key holes that is not a straight line between the key holes therewith forming an intermediate tab.

In at least one embodiment, the sheet material has formed therein at least one crease that delineates a first section and a second section, and wherein the interior key slot is formed in the first section and the intermediate key slots are formed in the section section.

In at least one embodiment, the sheet material further has at least one cut at the crease for improving the separability of the first section from the second section.

In at least one embodiment, the first section further has a scored line therein and wherein the crease and the at least one cut form a tab extending from the first section and having a length that when folded at the scored line traverses the interior key slot for locking the first section to a line inserted into the interior key slot.

There has thus been outlined, rather broadly, some of the features of invention in order that the detailed description thereof maybe better understood, and in order that the present artistic rendering may be better appreciated. There are additional features of the invention that will be described herein after.

In this respect, before explaining at least one embodiment of the invention in detail, it is to be understood that the invention is not limited in its application to the details of construction or to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

An object of at least one embodiment is to provide a means of identifying the contents of each piece of IV tubing and in determining the infusion parameters and IV access. Another object of at least one embodiment is to prevent adverse drug interaction.

Another object of at least one embodiment of the invention is to provide means to trace and identify intravenous lines and prevent IV medication mix up and medication errors.

Another object of at least one embodiment is to conveniently identify HIGH ALERT medications.

Another object of at east one embodiment is to prevent accidental bolus of IV medications.

Another object of at least one embodiment is to allow the IV the IV tag to pass through clamps and ports of the IV line.

Another object of at least one embodiment is to provide an economical and practical solution to the risk associated with multiple intravenous line infusion.

Another object of at least one embodiment is to provide a vehicle for greeting someone during personal events.

Other objects and advantages of the present invention(s) will become obvious to the reader and it is intended that these objects and advantages are within the scope of the present invention. To the accomplishment of the above related objects, this invention may be embodied in the form illustrated in the accompanying drawings, attention being called to the fact, however, that the drawings are illustrative only, and that changes may be made in the specific construction illustrated and described within the scope of this application.

DETAILED DESCRIPTION OF THE INVENTION

Figure 1:
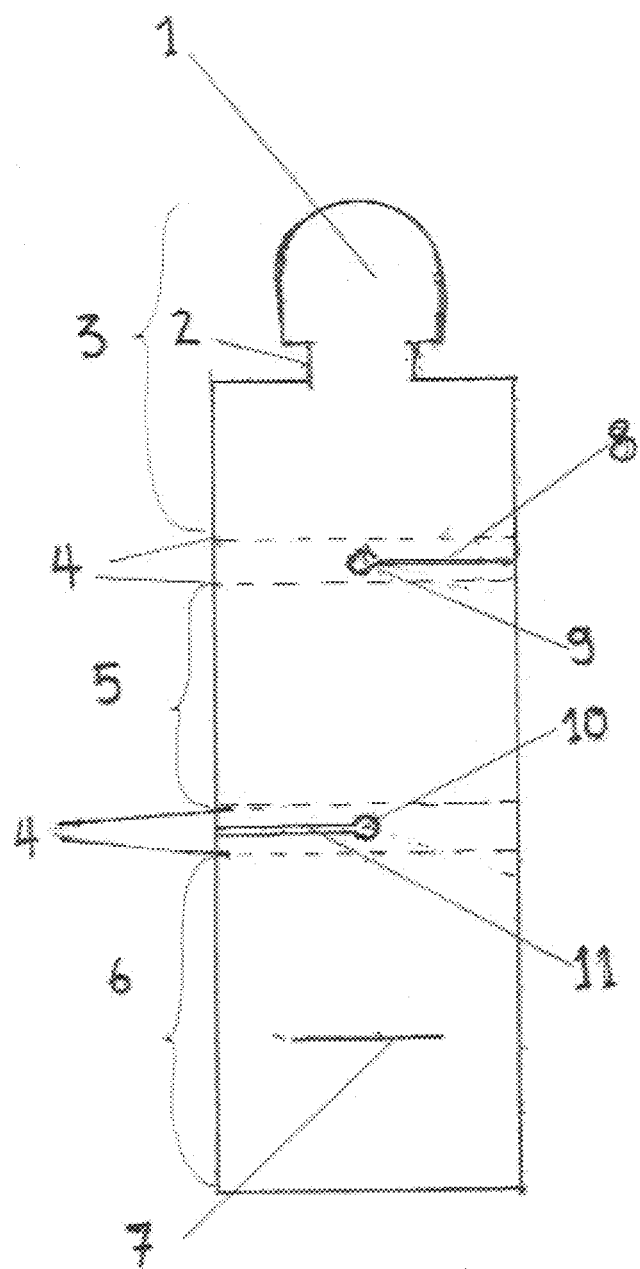
FIG. 1 is a frontal view of the unassembled locking line tag according to at least one embodiment of the invention or inventions described herein. The locking line tag may include an elongated rectangular sheet of plastic or paper material pre-folded or scored into three main parts.
Figure 2:
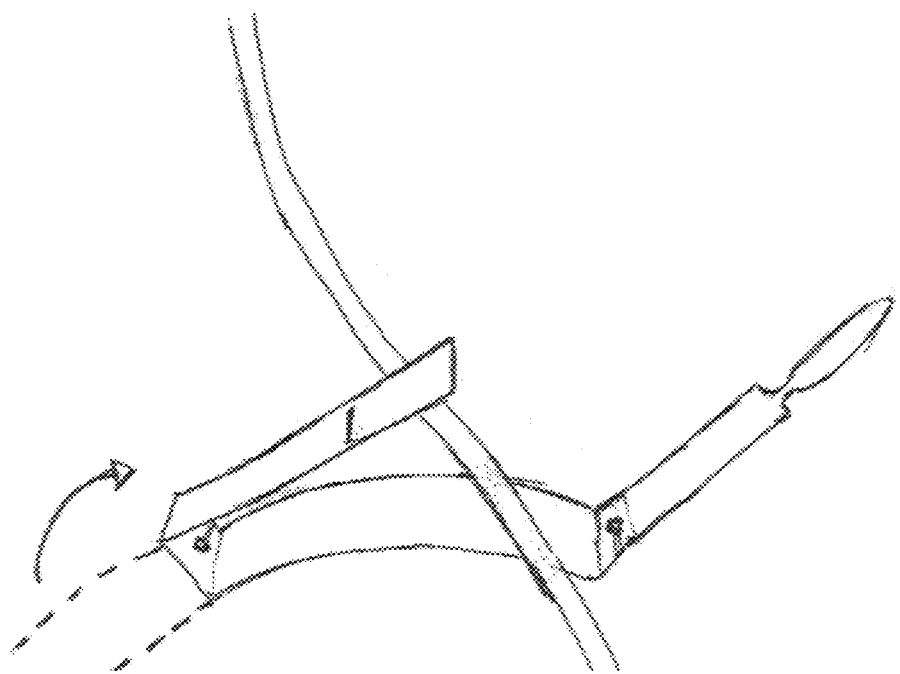
FIG. 2 is a lateral view of the locking line tag according to at least one embodiment of the present invention, showing the bottom flap first folded along the scored line or lines towards the center panel for placement about the IV line.
Figure 3:
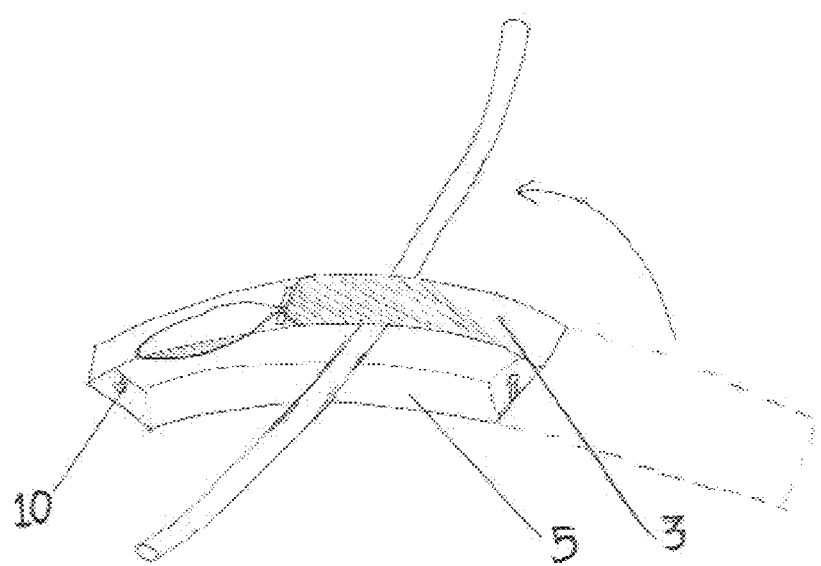
FIG. 3 is a lateral view of the locking line tag according to at least one embodiment of present invention, showing the top flap then folded along the scored lines towards the slit in the bottom flap for locking the two flaps together about the IV line.
Figure 4:
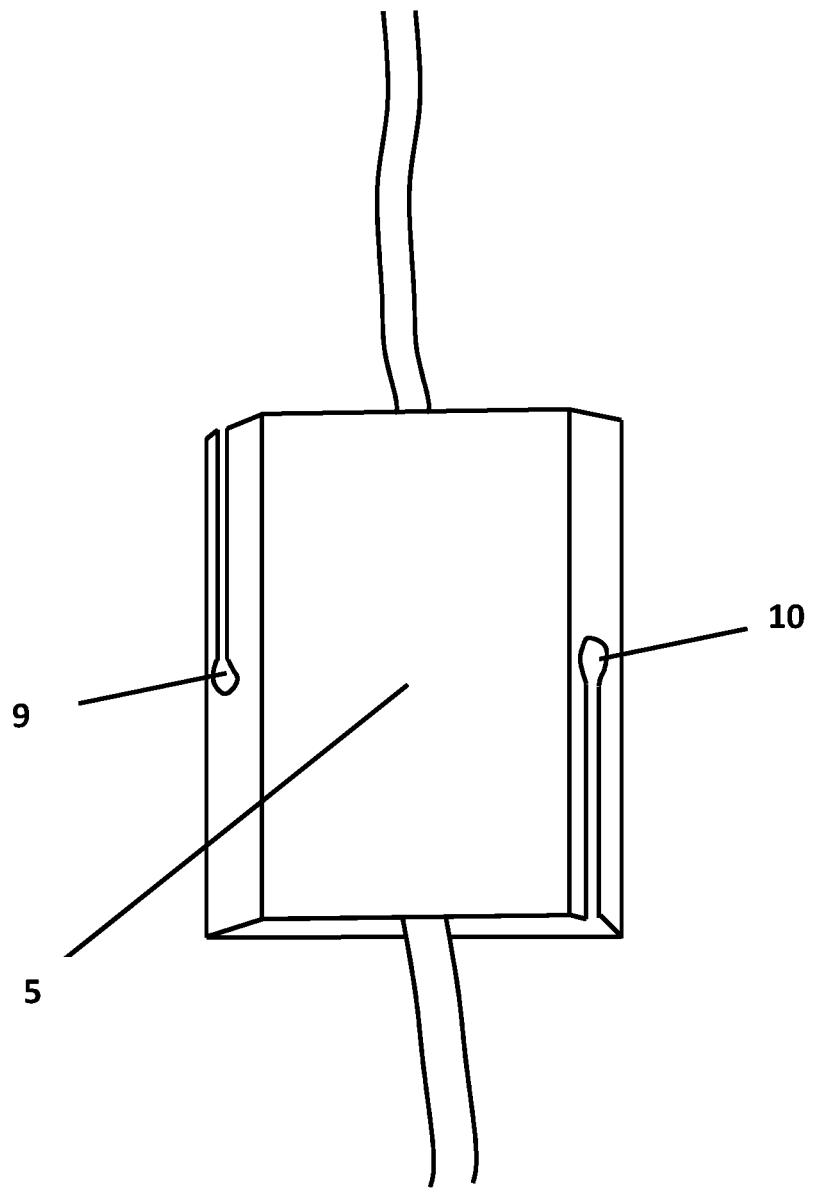
FIG. 4 is a view of the locking line tag according to at least one embodiment of present invention in a first orientation before locking the IV line. In this orientation, the user sharpens the creases at the score lines by pressing the folds with thumb and index finger, then fastens the top and bottom flap together with interlocking mechanism and/or adhesive.
Figure 5:
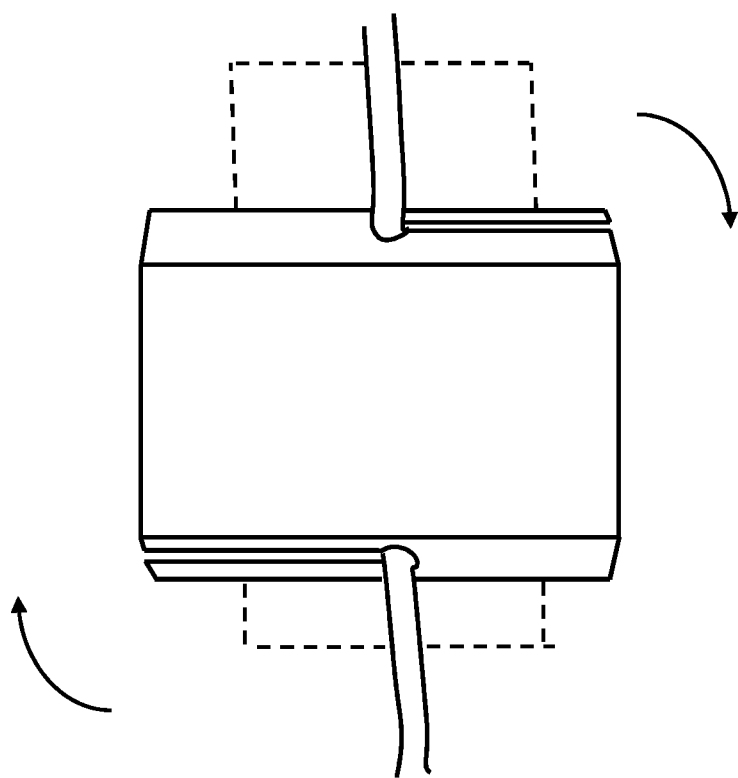
FIG. 5 is a view of the locking line tag according to at least one embodiment of present invention in a locking orientation on the IV line. The tri-fold forms a gap between the two flaps and the center panel, through which the IV line passes and is retained by a key opening therein.

Turning now descriptively to the drawings, in which similar reference characters denote similar elements throughout the several views, the figures illustrate an intravenous (IV) line tag which includes an elongated rectangular or other elongated shaped sheet of plastic or paper material folded to form a rectangular parallelepiped or similar structure and secured with a tape or preferably interlocking flaps to form a locking line tag.

Referring to FIGS. 1-20, The locking line tag will preferably include an elongated rectangular or other shaped sheet of plastic or paper material folded along a plurality of scores in the sheet material into rectangular or similarly shaped parallelepiped structure. This fold creates three sections, the top flap, center panel and bottom flap (3, 5, and 6), with a pair of key openings ((7, 8), (10, 11)), one in each of intermediate sections (4). The top panel includes a key tab (1, 2) and the bottom panel includes a corresponding slit (7) that receives and locks the key tab therein against being pulled apart. The central panel (5) may contain high alert label, name of drug, barcode, or any other information related to the drug being infused. The label may be preprinted or may define an areas to receive an adhesive label or for the user to write on. The top and bottom flaps (3, 6) interlock to form a "matchbox" or a rectangular or similar parallelepiped structure, as shown. The intravenous line key holes (9, 10) in the key openings keep the IV line in place, preferably via a friction fit, as shown in the accompanying drawings. The slits (8,11) allow the IV line to slide through, ending up in the holes (8, 9). As can be seen, each of the pair of slits communicates or is otherwise open at opposite ends of the structure. Although one pair key openings is shown in the figures, it is understood that several pairs of key openings may be formed into the structure to accommodate multiple IV lines. The dashed lines in the Figures represent scoring or creases that allow the panels to be folder into the pre-designed shape.

Figure 6:
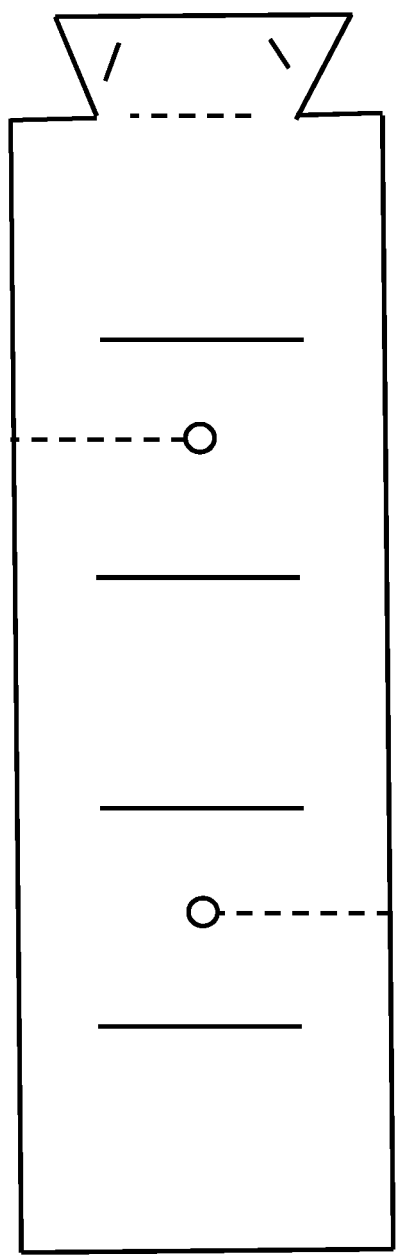
FIG. 6 is a frontal view of the unassembled locking line tag according to at least a second embodiment of the invention or inventions described herein.
Figure 7:
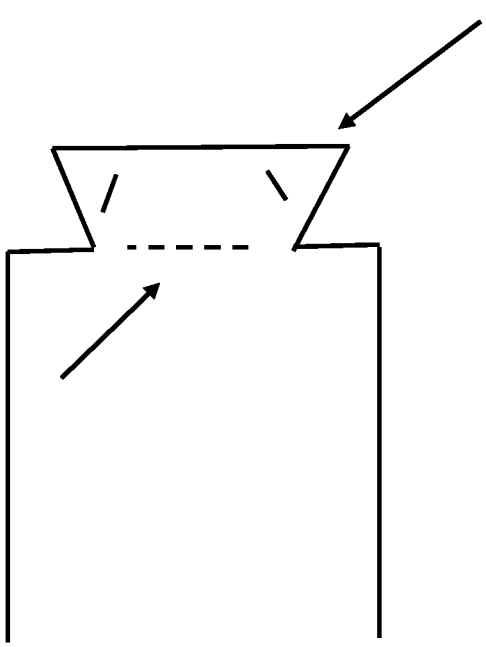
FIG. 7 is a detailed view of a locking mechanism of the second embodiment of the invention described herein.
Figure 8:
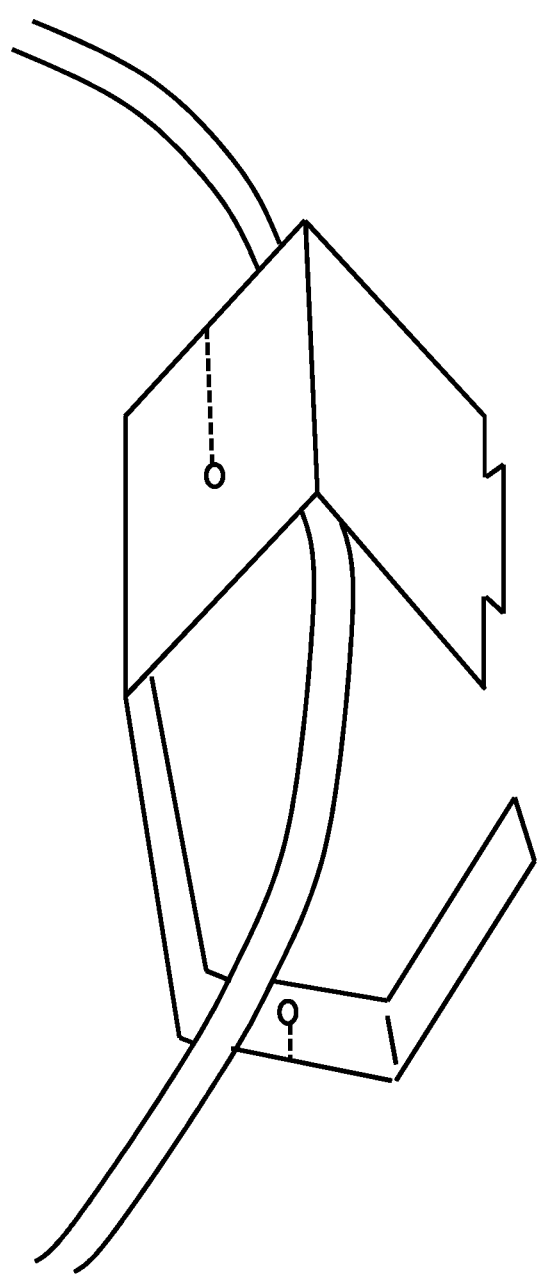
FIG. 8 is a lateral view of the locking line tag according to at least the second embodiment of the present invention, showing the bottom flap first folded towards the center panel for placement about the IV line.
Figure 9:
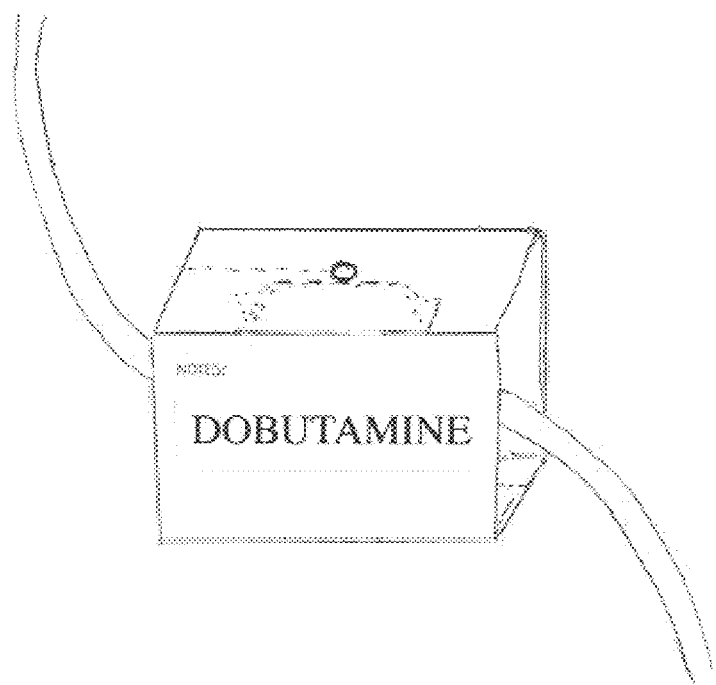
FIG. 9 is a view of the locking line tag according to at least the second embodiment of present invention in a first orientation before locking against the IV line.
Figure 10:
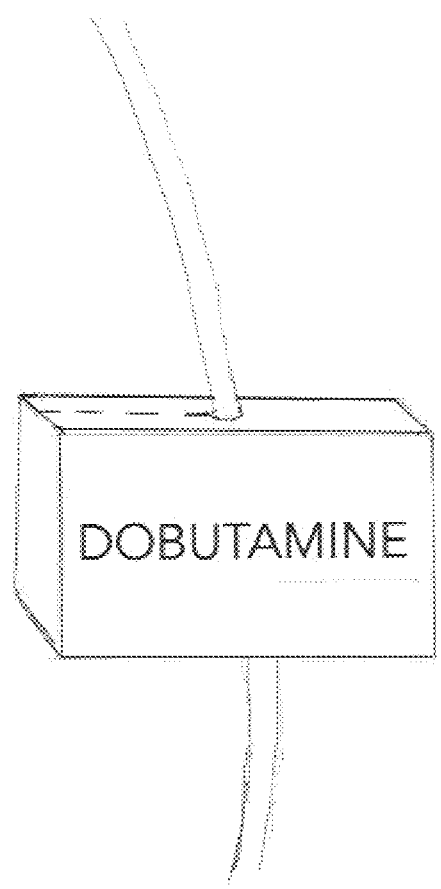
FIG. 10 is a view of the locking line tag according to at least the second embodiment of present invention in a locking orientation on the IV line.

Referring to FIG. 6, the top flap (1) may have a generally trapezoidal shape with a pair of wings extending therefrom that mate with a slit (7) that is about the length of the largest of the trapezoidal sides. As can be seen in FIG. 7, the wings may be folded for insertion into the slit (7) as shown in FIGS. 8-9. Once the rectangular parallelepiped is placed about the IV line, the structure may be rotated so that the IV line enters the key slits (8, 11) and rest finally in the key holes (9, 11), as shown in FIG. 10.

Figure 11:
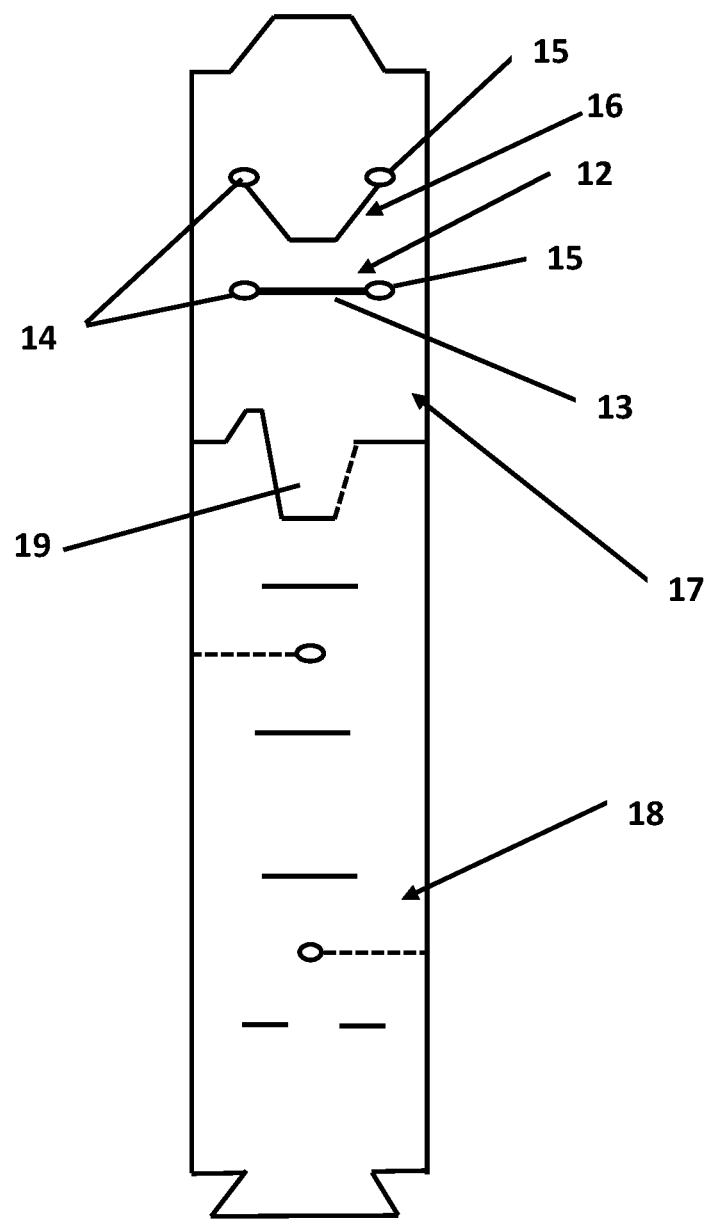
FIGS. 11-14 are views of the unassembled locking line tag according to at least a third embodiment of the invention or inventions described herein.
Figure 12:
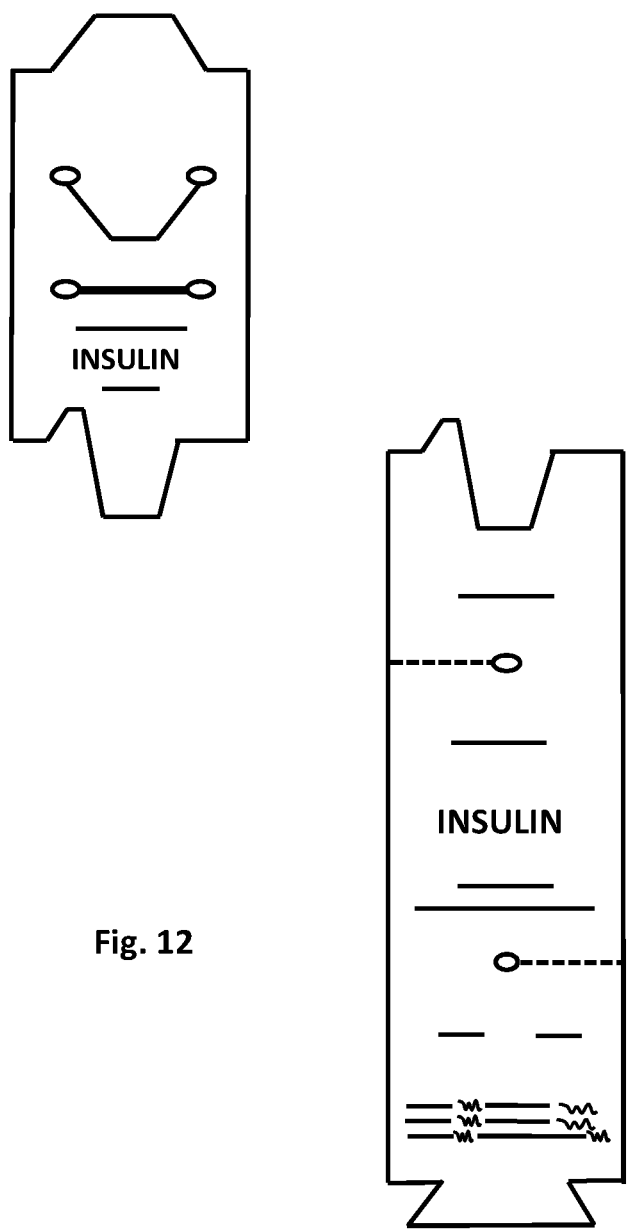
Figure 13:
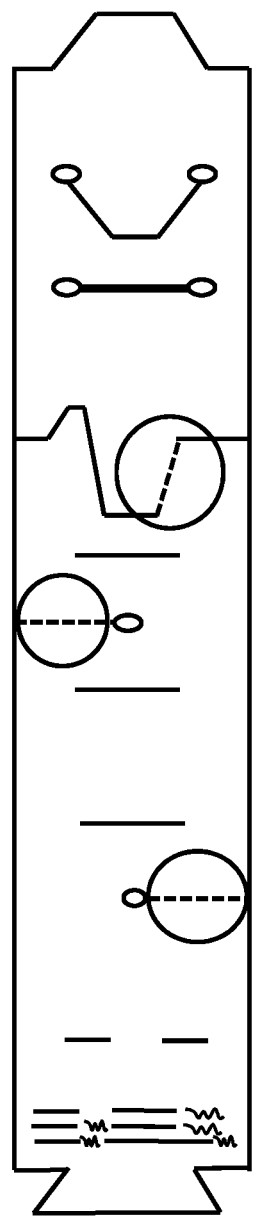

Referring to FIG. 11, the locking tag may further include one or more interior key slots (12), which are formed with a slit (13) between two key openings (14, 15). In the interior key slots, the slits do not open at any point on the perimeter of the structure. The slit (13) may be straight or a collection on indirect lines that form an intermediate tab (16). In at least one embodiment, the locking tag includes a first section (17) separable from a second section (18). In this regard, the user may separate the two sections for them to be used separately, as shown in FIG. 12. For example, the first section may be placed closer to the patient whereas the second section may be placed near the IV pump. The separability may be created with scores, cuts, or a combination thereof, which allow the user to tear the two parts apart and still maintain the desired shape in each of the separate parts, as shown.

Figure 14:
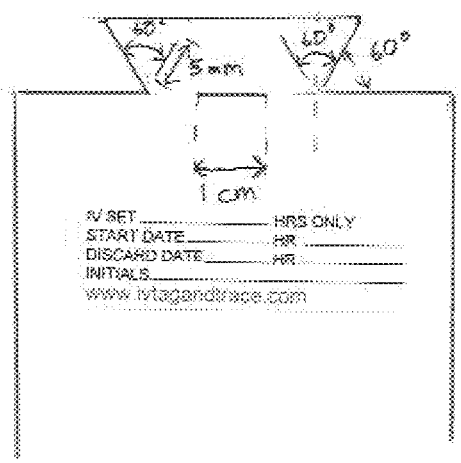

Referring to FIG. 14, the top flap may have wings triangular shaped and formed to be folder over to crate an equilateral triangle. The top flap may also include pre-printed areas for the user to provide details regarding the IV-line use.

Figure 15:
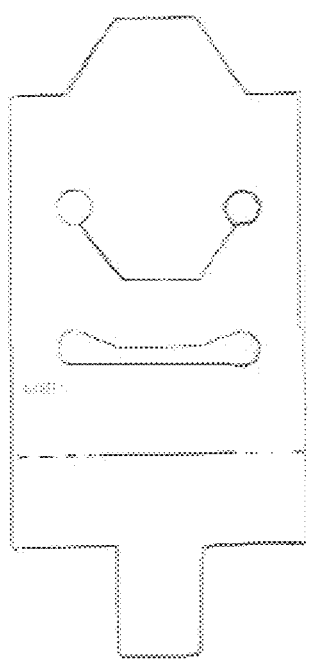
FIGS. 15-20 are views of the unassembled locking line tag according to at least a fourth embodiment of the invention or inventions described herein.
Figure 16:
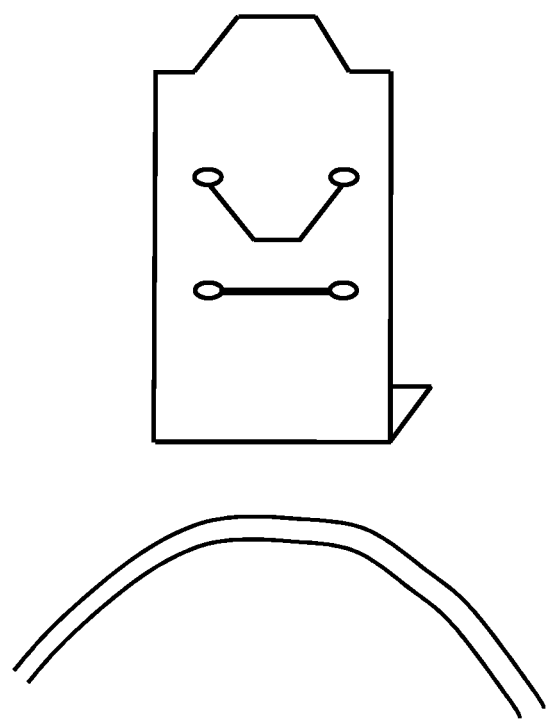
Figure 17:
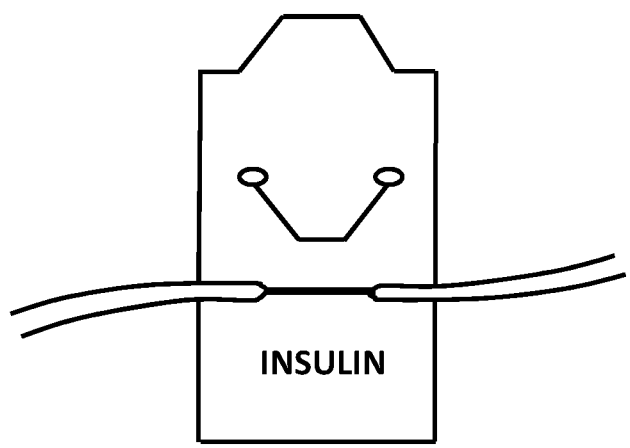
Figure 18:
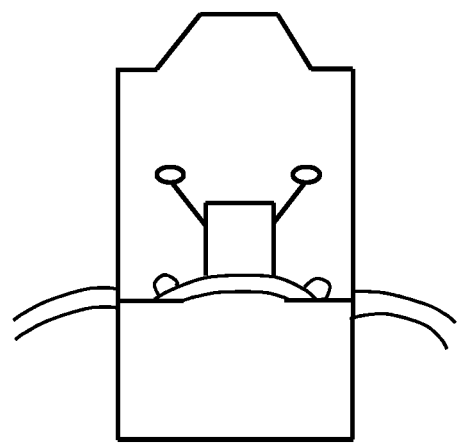
Figure 19:
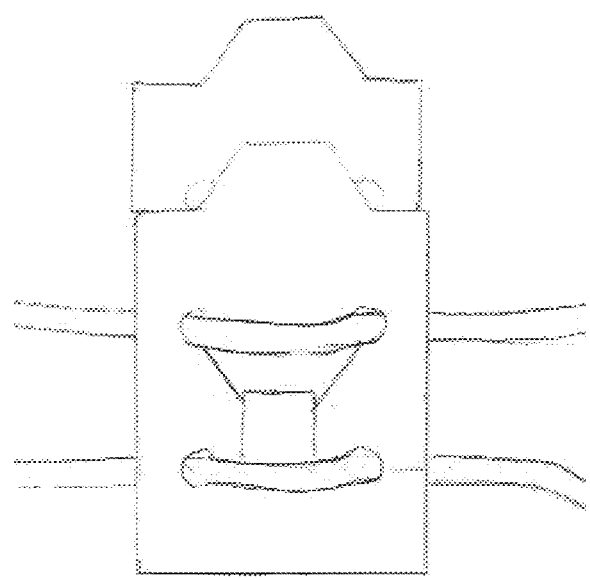
Figure 20:
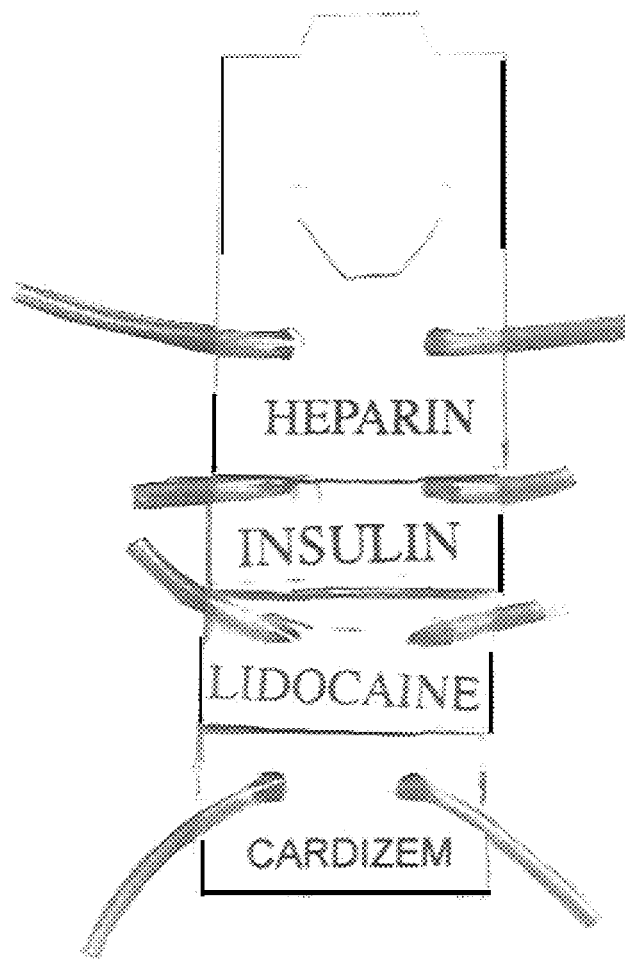

Referring to FIG. 15, the locking IV tag first section may further include one or more interior key slots (12) with a scored line for one to fold the first section at one end to create a section with a tab (19) extending therefrom. The height of the tab (19) is such that it traverses, when folded alone the scored line toward the rear, over the interior slot, as shown in FIGS. 16-18, to lock the IV-line into the tag. FIGS. 19-20 show multiple IV tags attached to each other, each labeled accordingly.

The present application provides a means of identifying IV medications by attaching the tag or tag sections to the IV line. The tag works by attaching the outside flaps either by taping or using interlocking mechanism to form a tubular structure through which the IV line passes. A ninety-degree twist secures the tag to the IV line with the opposing key slots formed therein. Twisting it back to the original position allows the tag to slide along the length of the line for the user to trace the IV line via gravity or otherwise. By twisting again, the tag locks anywhere along the IV line. The locking line tag may also be used commercially in greeting card industry. It can be used as a vehicle for greeting someone in a more personal setting like birthdays, get-well notes or anniversaries. These greeting tags can then be attached/anchored to balloon strings While the foregoing invention has been described in some detail for purposes of clarity and understanding, it will be appreciated by one skilled in the art, from a reading of the disclosure, that various changes in form and detail can be made without departing from the true scope of the invention.

What is claimed is:

1. A locking line tag comprising an elongated sheet of material having a top, bottom, and opposing lateral sides between the top and bottom, the sheet further having a plurality of scored lines therein that when folded form a tubular structure with a panel at each of the top and bottom ends that interlock with each other and at least a pair of intermediate sections, at least a first and a second of the intermediate sections having a key slot therein that open to opposing lateral sides of the locking tag, the locking line tag further having at least one interior key slot therein, wherein the sheet material has formed therein at least one crease that delineates a first section and a second section, the interior key slot is formed in the first section and the intermediate key slots are formed in the second section, the sheet material further having at least one cut at the crease for improving the separability of the first section from the second section, the first section further has a scored line therein, and wherein the crease and the at least one cut form a tab extending from the first section and having a length that when folded at the scored line traverses the interior key slot for locking the first section to a line inserted into the interior key slot.

2. The locking tag of claim 1, wherein the tubular structure is a rectangular parallelepiped.

3. The locking tag of claim 1, wherein the elongated sheet is generally rectangular.

4. The locking tag of claim 1, wherein the scored lines when folded form a tubular structure with at least three intermediate sections.

5. The locking tag of claim 4, wherein the key slots are located on a pair of non-adjacent intermediate sections.

6. The locking tag of claim 4, wherein the key slots are located on a pair of intermediate sections separated by one intermediate section.

7. The locking tag of claim 1, wherein the top panel comprises a key tab and the bottom panel comprises a slit configured to receive the key tab and lock the top and bottom panels to each other.

8. The locking tag of claim 1, wherein the key slots include a hole sized to create a friction fit with an IV line inserted into the key slot.

9. The locking tag of claim 1, wherein the interior key slot has a slit between a pair of key holes that is not a straight line between the key holes therewith forming an intermediate tab.

* * * * *